(12) United States Patent
Moritake et al.

(10) Patent No.: US 7,010,084 B1
(45) Date of Patent: Mar. 7, 2006

(54) LIGHT DETECTOR, RADIATION DETECTOR AND RADIATION TOMOGRAPHY APPARATUS

(75) Inventors: Masahiro Moritake, Tokyo (JP); George Edward Possin, Niskayuna, NY (US); Gregory Scott Zeman, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/920,464

(22) Filed: Aug. 18, 2004

(51) Int. Cl.
*G01N 23/08* (2006.01)
(52) U.S. Cl. .................. 378/19; 250/370.09
(58) Field of Classification Search ............ 378/98.8, 378/19, 4, 116; 250/369, 370.01, 370.08, 250/370.09, 370.11, 370.14, 208.1, 214.1, 250/214 R
See application file for complete search history.

(56) References Cited

U.S. PATENT DOCUMENTS

| | | | |
|---|---|---|---|
| 4,535,243 A | 8/1985 | Peschmann | |
| 5,041,729 A | 8/1991 | Takahashi et al. | |
| 5,420,452 A | 5/1995 | Tran et al. | |
| 6,144,718 A | 11/2000 | Hoffman et al. | |
| 6,512,809 B1 | 1/2003 | Doubrava et al. | |
| 6,522,715 B1 | 2/2003 | Hoffman et al. | |
| 6,671,347 B1 | 12/2003 | Tashiro et al. | |
| 6,707,046 B1 | 3/2004 | Possin et al. | |
| 2003/0226974 A1* | 12/2003 | Nomura et al. | 250/370.11 |
| 2004/0136493 A1* | 7/2004 | Konno et al. | 378/19 |

FOREIGN PATENT DOCUMENTS

JP 2000-060840 2/2000

* cited by examiner

*Primary Examiner*—David V. Bruce
*Assistant Examiner*—Hoon Song
(74) *Attorney, Agent, or Firm*—Carl B. Horton, Esq.; Armstrong Teasdale LLP

(57) ABSTRACT

A light detector includes a plurality of light receiving sections which are formed in a substrate and generate signal charges corresponding to the amount of incident light, and a plurality of wirings which are formed on the substrate and fetch the signal charges from the light receiving sections, wherein at least some of the plurality of wirings are disposed so as to overlap with other light receiving sections different from the light receiving sections connected to fetch the signal charges.

16 Claims, 8 Drawing Sheets

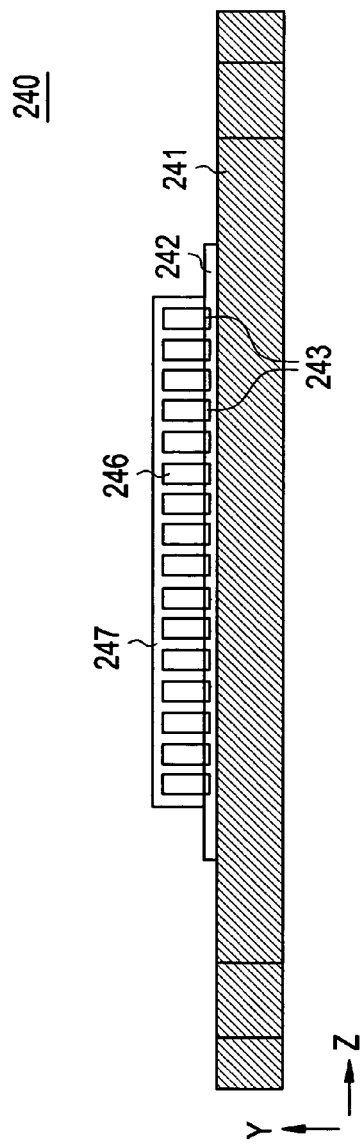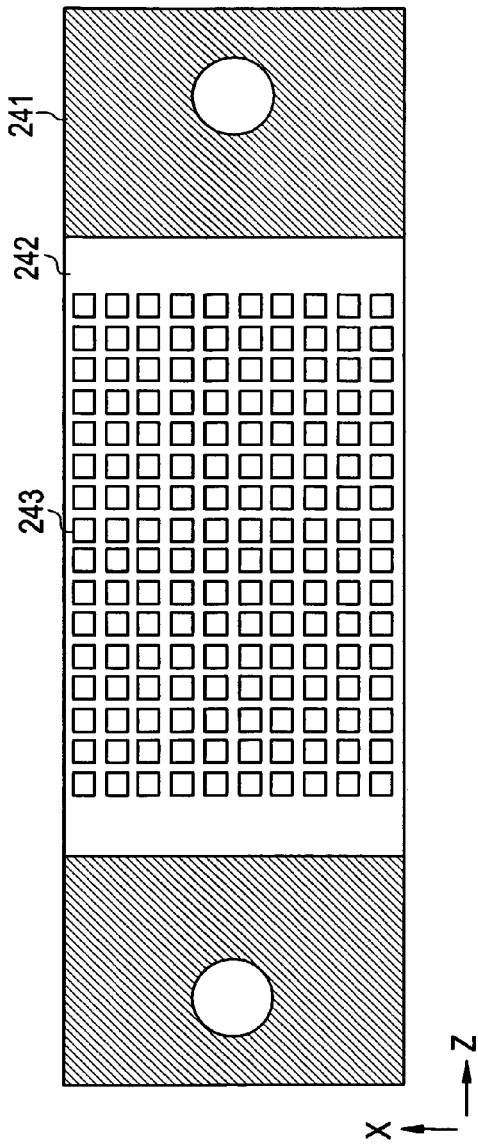

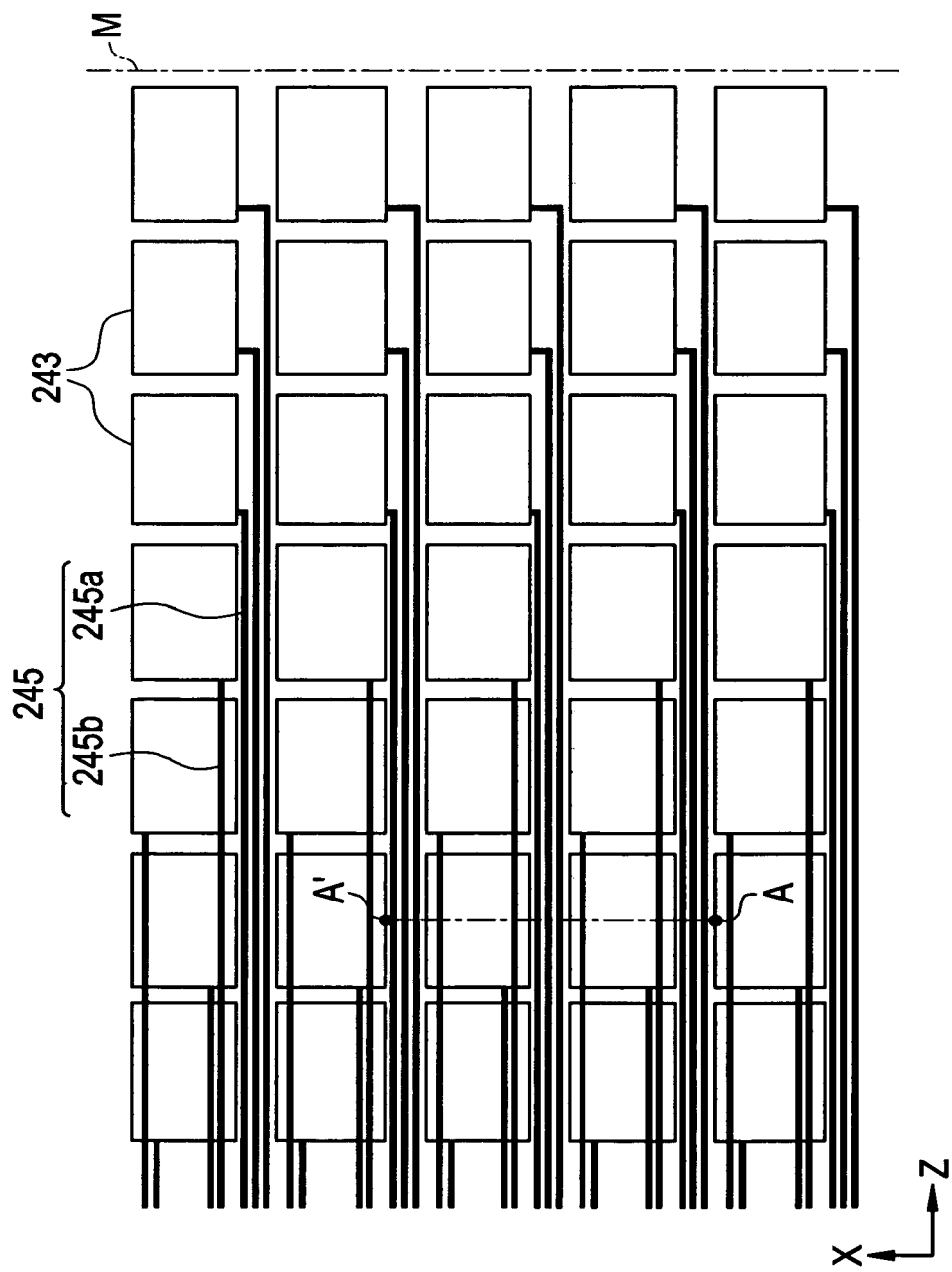

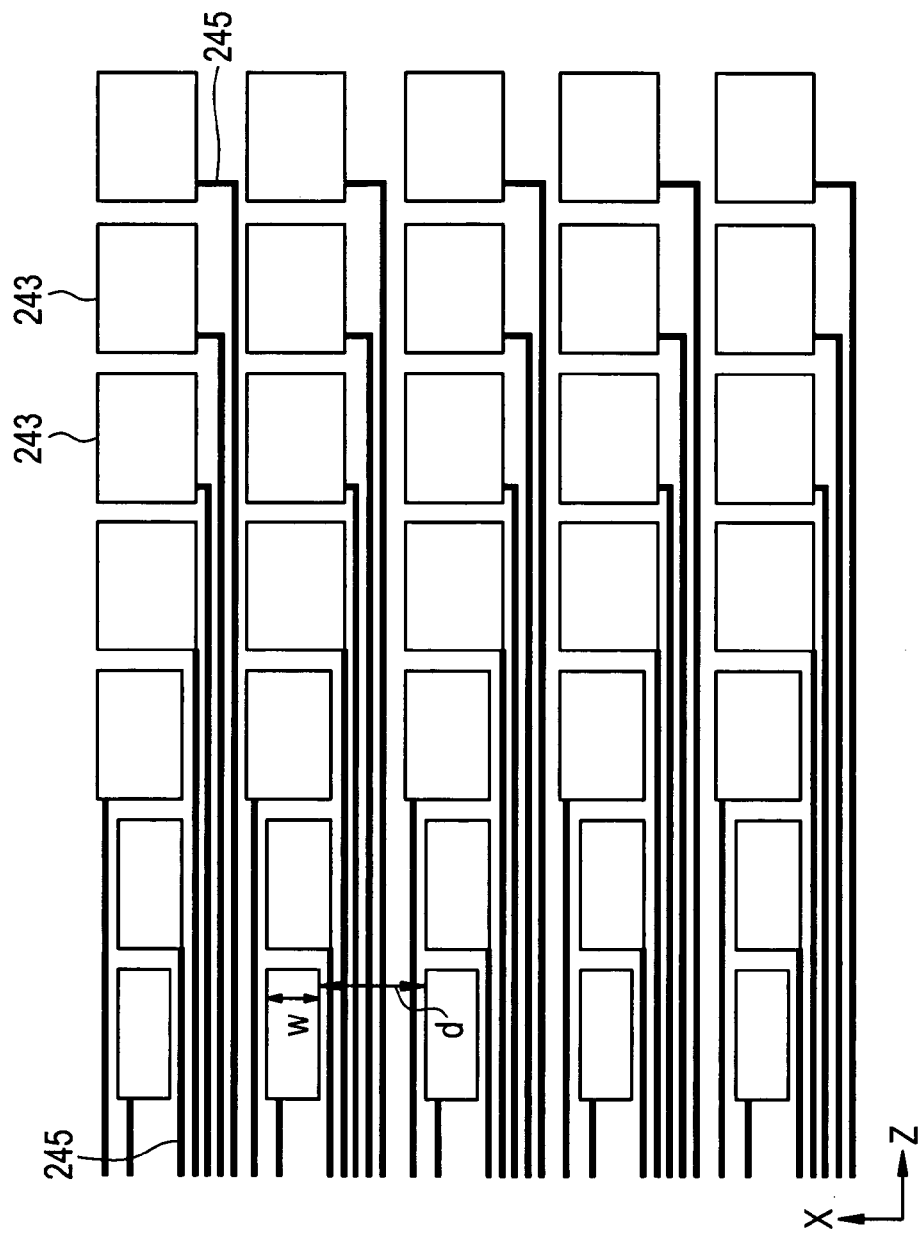

LIGHT DETECTOR, RADIATION DETECTOR AND RADIATION TOMOGRAPHY APPARATUS

BACKGROUND OF THE INVENTION

The present invention relates to a light detector, a radiation detector and a radiation tomography apparatus.

An X-ray detector wherein X-ray detection modules each formed with a plurality of photodiodes are provided side by side in plural form in a channel direction, has been used in a multi-slice type X-ray CT apparatus (refer to, for example, the following patent document 1).

FIG. 7 is a fragmentary plan view of a conventional X-ray detector. As shown in FIG. 7, a plurality of photodiodes 243 are disposed in matrix form in the X-ray detector, more specifically, one X-ray detection module of the X-ray detector. In the drawing, a z direction corresponds to a slice direction (body axial direction) and an x direction corresponds to a channel direction, respectively.

Since wirings (signal lines) 245 for fetching signal charges generated in the photodiodes 243 hardly pass light, they have heretofore been disposed in regions among the photodiodes 243 respectively.

Japanese Unexamined Patent Publication No. 2000-60840

However, the multi-slice type X-ray CT apparatus is accompanied by the problem that as the number of the photodiodes 243 in the slice direction (z direction) increases, the number of the wirings 245 that pass through the regions among the photodiodes arranged in the x direction increases, and there is hence a need to form fine wirings in the regions among the photodiodes 243, thereby causing a difficulty in its fabrication and a rise in its manufacturing cost.

Here, it is also considered that in view of a limit of wiring miniaturization or scale-down, as shown in FIG. 8, the interval d defined between adjacent photodiodes 243 arranged in an x direction is made wide and the width w of each photodiode 243 is made small. A problem, however, arises in that since the area of the photodiode 243 becomes small correspondingly, light detection efficiency is reduced.

SUMMARY OF THE INVENTION

Therefore, a first object of the present invention is to provide a light detector capable of suppressing a decrease in the area of a light receiving section with an increase in the number of wirings and thereby suppressing a reduction in light detection efficiency.

A second object of the present invention is to provide a radiation detector capable of suppressing a decrease in the area of a light receiving section with an increase in the number of wirings and thereby suppressing a reduction in radiation detection efficiency.

A third object of the present invention is to provide a radiation tomography apparatus capable of suppressing a decrease in the area of a light receiving section with an increase in the number of wirings and thereby suppressing a reduction in radiation detection efficiency.

In order to achieve the above objects, a light detector of the present invention comprises a plurality of light receiving sections which are formed in a substrate and generate signal charges corresponding to the amount of incident light, and a plurality of wirings which are formed on the substrate and fetch the signal charges from the light receiving sections. Some of the plurality of wirings are disposed so as to overlap with other light receiving sections different from the light receiving sections connected to fetch the signal charges.

In the light detector of the present invention, some of the plurality of wirings are disposed so as to overlap with other light receiving sections different from the light receiving sections connected to fetch the signal charges. The area of each light receiving section formed in the substrate is not limited by the wirings. Although the wirings shields the light from entering the light receiving sections, the light reaches the light receiving sections in regions other than the wirings, and thereby the signal charges corresponding to the amount of the incident light are generated by the light receiving units.

In order to achieve the above objects, a radiation detector of the present invention comprises a plurality of light receiving sections which are formed in a substrate and generate signal charges corresponding to the amount of incident light, a plurality of wirings which are formed on the substrate and fetch the signal charges from the light receiving sections, and scintillators which are provided on the light receiving sections of the substrate and emit lights each having a wavelength longer than that of radiation in accordance with the incidence of the radiation. Some of the plurality of wirings are disposed so as to overlap with other light receiving sections different from the light receiving sections connected to fetch the signal charges.

In the radiation detector of the present invention, some of the plurality of wirings are disposed so as to overlap with other light receiving sections different from the light receiving sections connected to fetch the signal charges. The area of each light receiving section formed in the substrate is not limited by the wirings. Although the wirings shields the lights emitted from the scintillators in accordance with the incidence of the radiation from entering the light receiving sections, the lights reach the light receiving sections in regions other than the wirings and thereby the signal charges corresponding to the amount of the incident light are generated by the light receiving sections.

In order to achieve the above objects, a radiation tomography apparatus of the present invention comprises radiation irradiating means which irradiates a subject with radiation, and a radiation detector which detects the radiation transmitted through the subject. The radiation detector includes a plurality of light receiving sections which are formed in a substrate and generate signal charges corresponding to the amount of incident light, a plurality of wirings which are formed on the substrate and fetch the signal charges from the light receiving sections, and scintillators which are provided on the light receiving sections of the substrate and emit lights each having a wavelength longer than that of the radiation in accordance with the incidence of the radiation. Some of the plurality of wirings are disposed so as to overlap with other light receiving sections different from the light receiving sections connected to fetch the signal charges.

In the radiation tomography apparatus of the present invention, some of the plurality of wirings connected to the light receiving sections of the radiation detector are disposed so as to overlap with other light receiving sections different from the light receiving sections connected to fetch the signal charges, and the area of each light receiving section formed in the substrate is not limited by the wirings. The radiation is launched into the subject by the radiation irradiating means. The radiation transmitted through the subject is launched into the scintillators of the radiation detector. Although the wirings shields the lights emitted from the scintillators in accordance with the incidence of the radiation from entering into the light receiving sections, the lights reach the light receiving sections in regions other than the wirings, and thereby the signal charges corresponding to the amount of the incident light are generated by the light receiving sections.

According to the light detector of the present invention, it is possible to suppress a decrease in the area of each of light receiving sections with an increase in the number of wirings and thereby suppress a reduction in light detection efficiency. According to the radiation detector of the present invention, it is possible to suppress a decrease in the area of each of light receiving sections with an increase in the number of wirings and thereby suppress a reduction in radiation detection efficiency. According to the radiation tomography apparatus of the present invention, it is possible to suppress a decrease in the area of each of light receiving sections with an increase in the number of wirings and thereby suppress a reduction in radiation detection efficiency. Further objects and advantages of the present invention will be apparent from the following description of the preferred embodiments of the invention as illustrated in the accompanying drawings.

BRIEF DESCRIPTION OF THE DRAWINGS

FIG. 3(a) is a cross-sectional view of one X-ray detection module as view in a y-z plane, and FIG. 3(b) is a plan view of the X-ray detection module, respectively.

FIG. 4 is a plan view for describing the layout of photodiodes and wirings formed in a substrate.

FIG. 8 is a fragmentary plan view for describing problems of the conventional X-ray detector with an increase in the number of wirings.

DETAILED DESCRIPTION OF THE INVENTION

Embodiments of the present invention will hereinafter be described with reference to the accompanying drawings.

Figure 1:
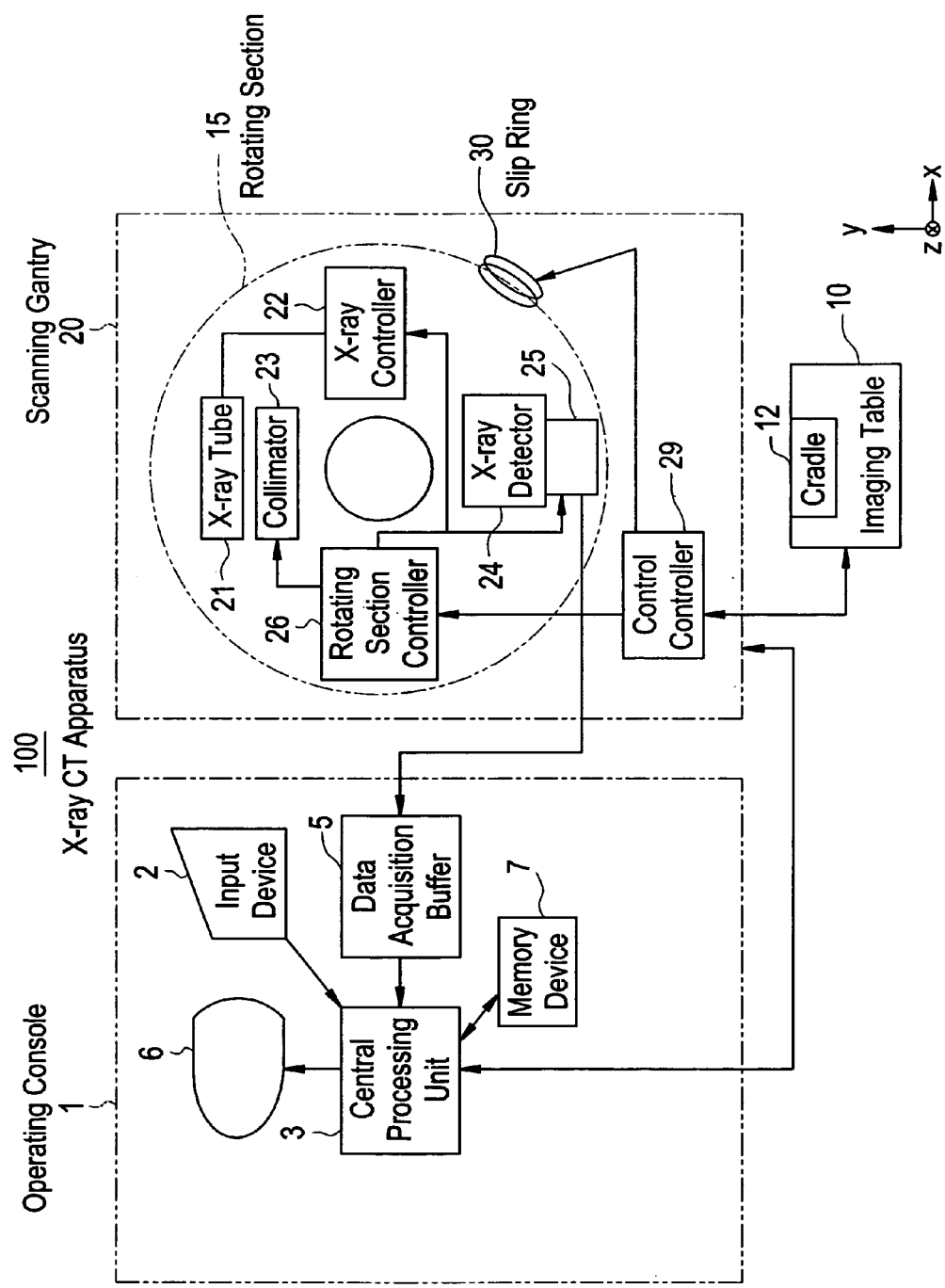
FIG. 1 is a schematic configurational view of a radiation tomography apparatus according to the present embodiment.

FIG. 1 is a schematic configurational view of a radiation tomography apparatus (X-ray CT apparatus) according to an embodiment. The X-ray CT apparatus 100 according to the present embodiment is equipped with an operating console 1, an imaging table 10 and a scanning gantry 20.

The operating console 1 is provided with an input device 2 which receives an input from an operator, a central processing unit 3 which executes an image reconstructing process or the like, a data acquisition buffer 5 which collects projection data obtained by the scanning gantry 20, a CRT 6 which displays a CT image reconstructed from the projection data, and a memory device 7 which stores programs, data and an X-ray CT image therein.

The imaging table 10 includes a cradle 12 which carries a subject placed thereon in a bore (cavity portion) of the scanning gantry 20 and carries out it therefrom. The cradle 12 is elevated by a motor built in the imaging table 10 and moves linearly along the table.

The scanning gantry 20 is provided with an X-ray tube (X-ray irradiating means) 21, an X-ray controller 22, a collimator 23, an X-ray detector (radiation detector) 24, a data acquisition system (DAS) 25, a rotating section controller 26 which rotates the X-ray tube 21 or the like about a body axis of the subject, and a control controller 29 which performs a transfer of a control signal or the like between the operating console 1 and the imaging table 10.

A configuration of the X-ray CT apparatus according to the present embodiment is generally as described above. In the X-ray CT apparatus having the above configuration, the collection of projection data is performed in the following manner, for example.

The position of the subject as viewed in a z-axis direction is fixed in a state in which the subject is placed in the cavity portion of a rotating section 15 of the scanning gantry 20. An X-ray beam from the X-ray tube 21 is applied to the subject (projection of X-rays), and the X-rays transmitted through the subject are detected by the X-ray detector 24. Then, the detection of the transmitted X-rays is performed such that data corresponding to 360° are collected in directions of plural N (e.g., N=1,000) views while the X-ray tube 21 and the X-ray detector 24 are being rotated about the subject (i.e., a projection angle (view angle) is being changed).

The detected respective transmitted X-rays are converted into digital values by the DAS (Data Acquisition System) 25, which in turn are transferred to the operating console 1 via the data acquisition buffer 5 as projection data. This operation is called "one scan". A scan position is sequentially moved a predetermined amount in the z-axis direction (slice direction and body axial direction) and the next scan is performed. Such a scan system is called a conventional scan system (or axial scan system). However, a system for moving the imaging table 10 at a predetermined speed in synchronization with a change in the projection angle and collecting projection data while a scan position is being moved (the X-ray tube 21 and the X-ray detector 24 helically orbit around the subject), is referred to as a so-called helical scan system. The present invention can be applied even to both of the conventional scan system and the helical scan system.

The operating console 1 stores the projection data transferred from the scanning gantry 20 in the memory device 7. Further, the operating console 1 performs, for example, a predetermined reconstruction function and a superposition arithmetic operation and thereby reconstructs a tomographic image according to a back projection process. Here, the operating console 1 is capable of reconstructing a tomographic image in real time on the basis of the projection data sequentially transferred from the scanning gantry 20 during scan processing and always displaying the latest tomographic image on the CRT 6. Further, the operating console 1 invokes the projection data stored in the memory device 7 to thereby enable an image reconstruction anew.

Figure 2:
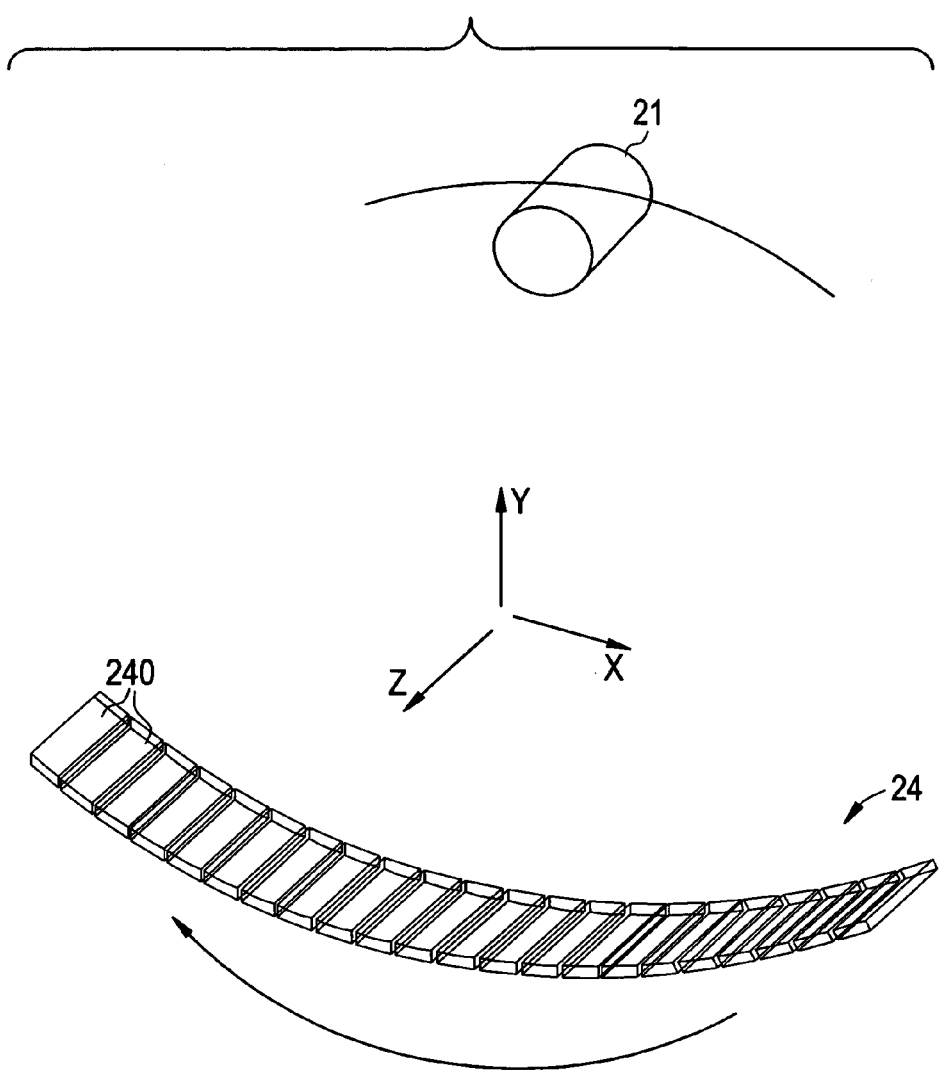
FIG. 2 is a view showing detailed configurations of an X-ray tube and an X-ray detector.

FIG. 2 is a diagram showing detained configurations of the X-ray tube 21 and the X-ray detector 24.

As shown in FIG. 2, the X-ray detector 24 is configured in such a manner that a plurality of X-ray detection modules 240 are arranged on a circular arc with the X-ray tube 21 as the center. As described above, the X-ray tube 21 and the X-ray detector 24 rotate around the subject within an x-y plane, for example. In the specification of the present application, the positional relationship between the X-ray detection modules 240 at the central portion of the X-ray detector 24 is used to refer to an arcuate direction, i.e., an x direction of the X-ray detector 24 as a channel direction. Incidentally, the z direction corresponds to the slice direction (body axial direction).

FIG. 3(a) is a cross-sectional view of one X-ray detection module 240 as viewed in a y-z plane, and FIG. 3(b) is a plan view of the X-ray detection module 240, respectively.

As shown in FIG. 3, the X-ray detection module 240 is configured in such a manner that a substrate 242 made up of silicon or the like is attached onto a central portion of a circuit board 241 comprising a ceramic board formed with wirings, for example.

The substrate 242 is formed with photodiodes 243 in matrix form. Each of the photodiodes 243 comprises a p type impurity region formed in an n-type substrate 242, for example. A signal charge corresponding to the amount of incident light is generated within the substrate and captured by the corresponding photodiode 243.

Scintillators 246 fixed to the substrate 242 with an unillustrated transparent adhesive interposed therebetween are provided over the substrate 242 so as to correspond to the photodiodes 243 respectively. Each of the scintillators 246 comprises a fluorescent material which reacts with an incident X-ray and thereby generates light having a wavelength longer than that of an X-ray, i.e., light in a substantially visible region which enables the generation of a signal charge by the photodiode.

A reflection layer 247 is formed so as to cover the scintillators 246 on the X-ray incident side from above and between the scintillators 246. The reflection layer 247 is made up of, for example, $TiO_2$ which causes the X-rays to pass therethrough and reflects lights emitted from the scintillators 246.

Interconnections or wirings to be described later formed in the substrate 242 are drawn out to both ends of the substrate 242 and connected to their corresponding circuits of the circuit board 241 at both ends by wires.

FIG. 4 is a plan view for describing the layout of the photodiodes 243 and wirings 245 formed in the substrate 242.

As shown in FIG. 4, the wirings 245 made of aluminum or the like are connected to their corresponding photodiodes 243 to fetch signal charges from the photodiodes 243 arranged in matrix form. The wirings 245 are formed between the photodiodes 243 and the scintillators 246 respectively. Although only one side, i.e., the left side of a boundary line M at the central portion of a matrix of the photodiodes 243 is illustrated in FIG. 4, photodiodes 243 are arranged even on the right side in a manner similar to it.

On the one side (left side) of the boundary line M, the wirings 245 respectively connected to the photodiodes 243, which have been arranged in matrix form, are drawn to the left end (one end) of the substrate 242. The wirings 245 are roughly divided into wirings 245a disposed between the photodiodes 243 and wirings 245b disposed so as to overlap with other photodiodes 243. Incidentally, particularly when it is not necessary to distinguish between the wirings 245a and the wirings 245b, they are simply called the wirings 245.

In the present embodiment, the wirings connected to the photodiodes 243 on the center side (side close to the boundary line M) of the matrix extend in a z direction among the photodiodes 243 arranged in a column direction (x direction) and are drawn to the end of the substrate 242.

The wirings 245b connected to the photodiodes 243 on the end side of the matrix extend in the z direction so as to overlap with the photodiodes 243 adjacent to one another in the z direction and are drawn to the end of the substrate 242.

Incidentally, although not shown in the drawing, wirings 245 respectively connected to the photodiodes 243 are drawn to the other end (right end) of the substrate in like manner even on the other side, i.e., right side of the boundary line M at the central portion of the matrix.

Figure 5:
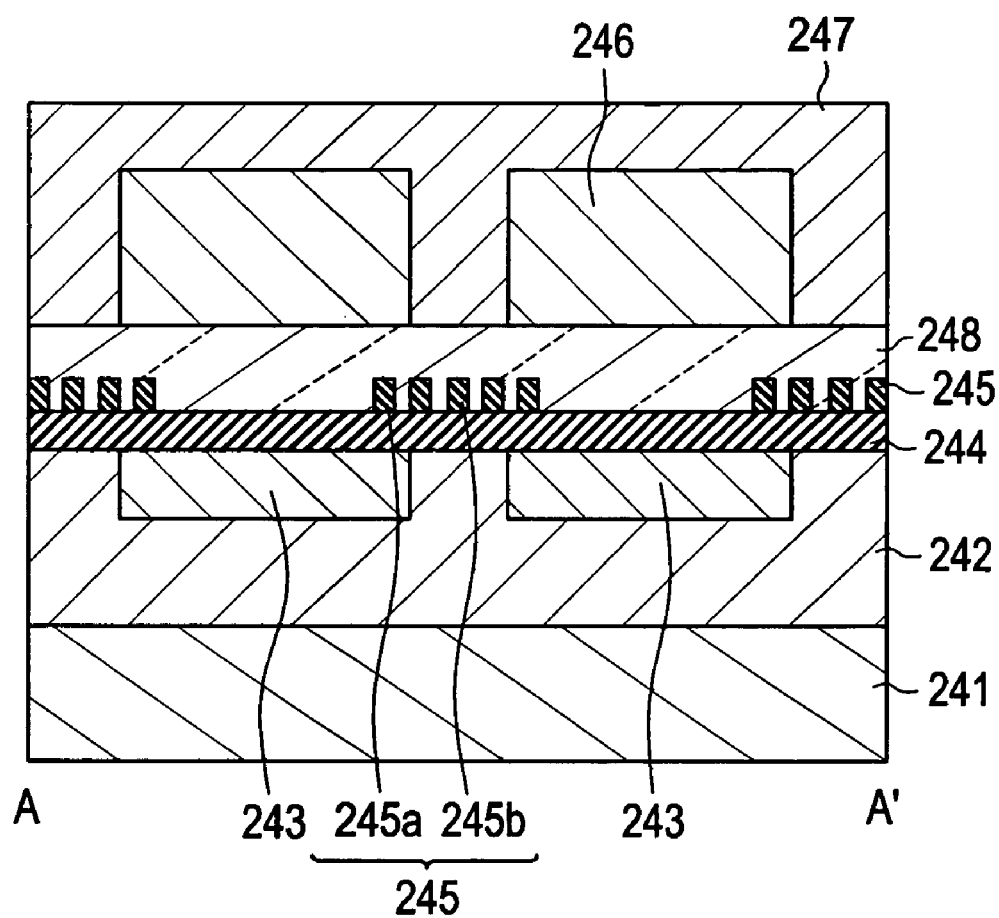
FIG. 5 is a cross-sectional view corresponding to line A-A' of FIG. 4.

FIG. 5 is a cross-sectional view corresponding to line A-A' of FIG. 4.

As shown in FIG. 5, photodiodes 243 each comprising a p-type impurity region are formed in a substrate 242 on a circuit board 241, which is made of n-type silicon, for example. Incidentally, described more specifically, a region with a pn junction as the center serves as a photodiode.

An insulating film 244 made of, for example, silicon oxide or the like is formed over the photodiodes 243, and wirings 245 are formed over the insulating film 244. The insulating film 244 holds insulation between the photodiodes 243 other than those intended for connection and the wirings 245.

Scintillators 246 are fixed onto the substrate 242 formed with the wirings 245 with a transparent adhesive 248 interposed therebetween, and a reflection layer 247 is formed so as to cover the scintillators 246.

As shown in FIG. 5, some wirings 245b of the wirings 245, which are respectively located between the photodiodes 243 and the scintillators 246, are formed over the photodiodes 243, whereas the other wirings 245a thereof are formed over a region between the adjacent photodiodes 243 and 243.

Figure 6A:
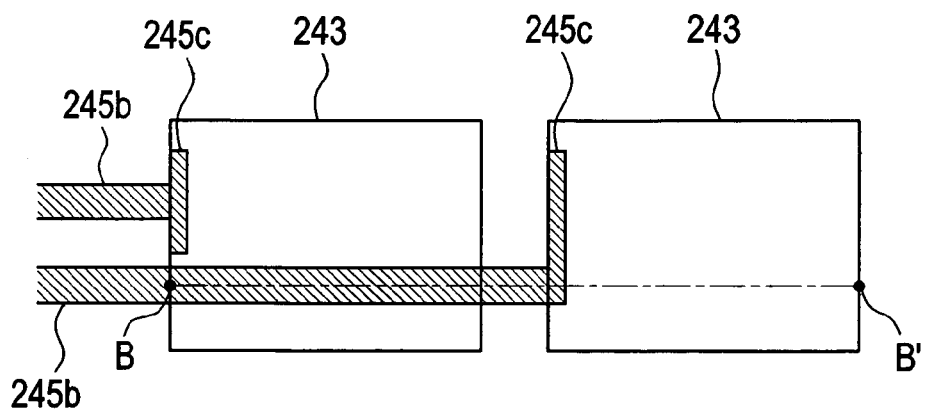
FIG. 6(a) is a fragmentary plan view for describing connections of wirings and photodiodes.
Figure 6B:
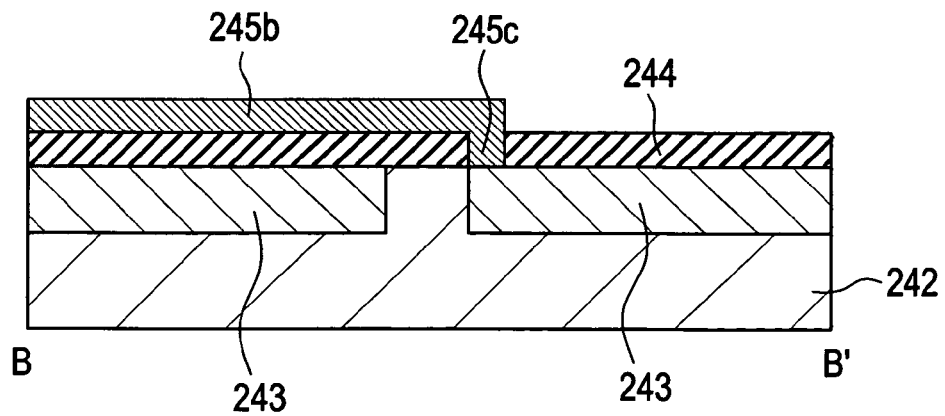
FIG. 6(b) is a cross-sectional view taken along line B-B' of FIG. 6(a), respectively.
Figure 7:
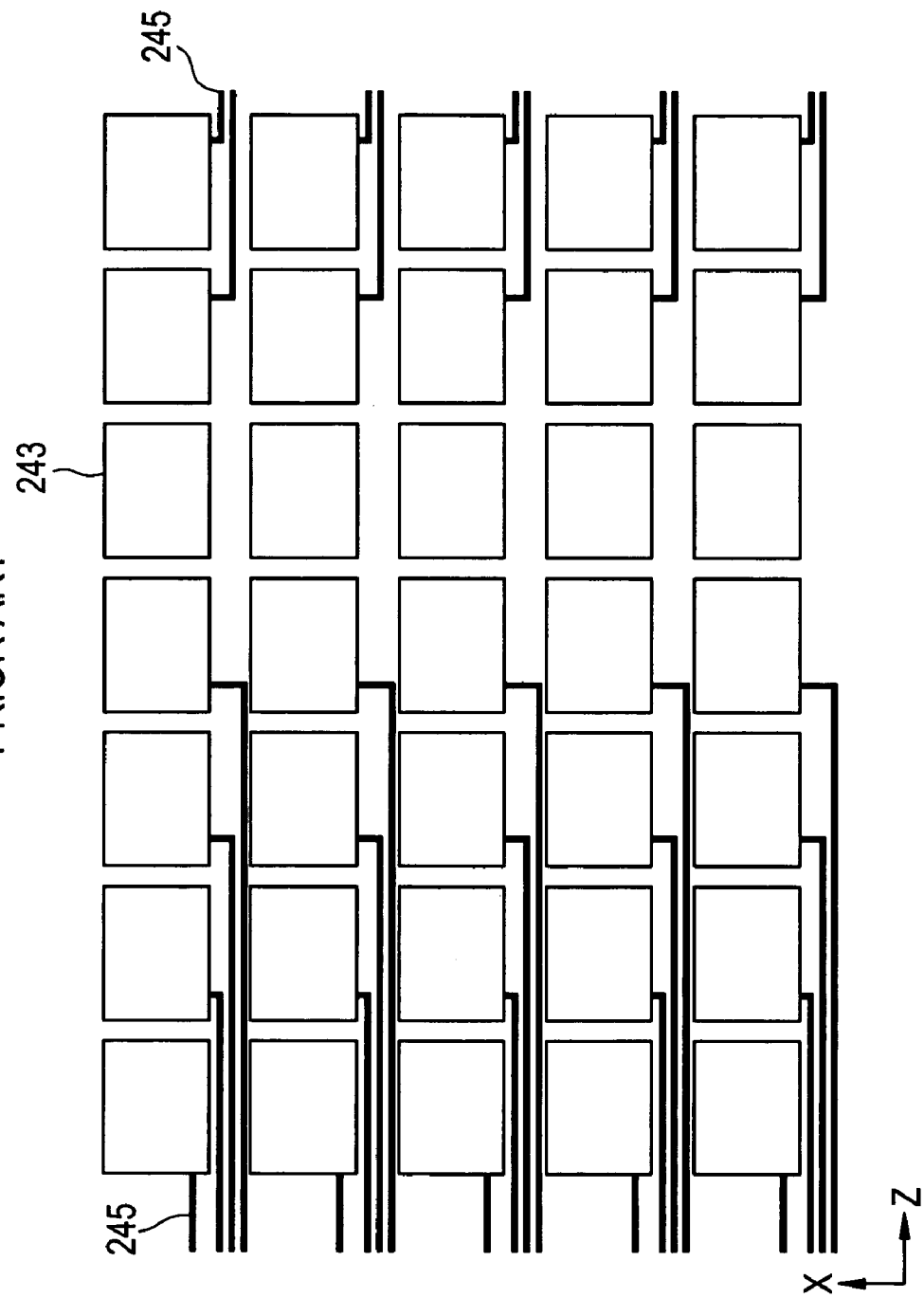
FIG. 7 is a fragmentary plan view of a conventional X-ray detector.

FIG. 6(a) is a fragmentary plan view for describing connections between wirings and photodiodes, and FIG. 6(b) is a cross-sectional view taken along line B-B' of FIG. 6(a), respectively.

As shown in FIG. 6, connecting holes are defined in an insulating film 244 lying over photodiodes 243, and a wiring material such as aluminum is embedded into each of the connecting holes, whereby connecting portions 245c for connecting wirings 245 and their corresponding photodiodes 243 are formed.

The connecting portions 245c may be configured integrally with the wirings 245b made of aluminum or the like. Alternatively, the connecting portions 245c may be constituted of a material different from the wiring material so as to be embedded into the connecting holes. Incidentally, the connections of wirings 245a and their corresponding photodiodes 243 are also similar to the above.

The operation of the X-ray detector 24 will be explained.

X-rays, which pass through a subject and are thereby decayed, are launched into their corresponding scintillators 246, so lights are emitted from the scintillators 246. The lights emitted from the scintillators 246 enter the photodiodes 243.

When the lights enter into the photodiodes 243, signal charges are produced, which in turn are captured by the photodiodes 243. The signal charges captured by the photodiodes 243 are fetched out to the end of the substrate 242 through the wirings 245, followed by being transmitted to a detection circuit of the circuit board 241 via the wires.

Since the X-ray detection modules 240 are arranged in large numbers adjacent to one another in the channel direction (x direction) as shown in FIG. 2, the signal charges are taken out every channels in the z direction (slice direction) different from their arrangement or layout direction (x direction).

Since the light input is smaller because of structure of scintillator 246 and reflector 247 and also the probability that the signal charge will reach the region of each photodiode 243 is low even if the signal charge occurs, in the region between the photodiode 243 and the photodiode 243 upon the operation of the X-ray detector 24, light is not detected very efficiently. Thus, the area of the photodiode 243 may preferably be wide to capture the signal charge produced in the photodiode 243 with efficiency.

When it is necessary to form the number of wirings larger than the number of wirings reasonably formable in the regions among the photodiodes 243, the wirings are caused to lead so as to overlap with the peripheral photodiodes 243 and configured so as to take out the signal charges in the z direction (slice direction).

Thus, since the photodiodes 243 exist among the wirings, although the light is cut off by the wirings per se, the detection of light at their portions is ensured. Therefore, fine or narrow wirings are no longer used at random and a reduction in light detection efficiency can be suppressed to the minimum.

The reflection layer 247 is formed so as to cover the scintillators 246. Therefore, if the light is reflected by each of the wirings 245b on the photodiodes 243, the light is reflected by the reflection layer 247 and enters each photodiode 243. Thus, it is possible to prevent a reduction in light detection efficiency due to the existence of the wirings 245b on the photodiodes 243.

As shown in FIG. 4, the wirings connected to the photodiodes 243 on the center side (side close to the boundary line M) of the matrix are placed so as to extend in the z direction among the photodiodes 243 by priority. Further, the wirings 245b connected to the photodiodes 243 on the end side of the matrix are disposed in the form extended in the z direction so as to overlap with the photodiodes 243 adjacent to one another in the z direction, whereby the number of the photodiodes 243 on which the wirings 245b are superimposed, can be suppressed as much as possible. Therefore, it is possible to suppress a reduction in light detection efficiency due to the wirings 245b.

According to a radiation detector according to the present embodiment, as described above, it is possible to suppress a reduction in the area of a light receiving section with an increase in the number of wirings and suppress a decrease in radiation detection efficiency. Thus, according to a radiation tomography apparatus that adopts the radiation detector according to the present embodiment, it is possible to suppress a reduction in the area of a light receiving section with an increase in the number of wirings and suppress a decrease in radiation detection efficiency.

The present invention is not limited to the description of the present embodiment. Although the present embodiment has explained the radiation detector and the radiation tomography apparatus, the present invention is applicable even to a light detector free of scintillators. Even in this case, it is possible to suppress a decrease in the area of a light receiving section with an increase in the number of wirings and suppress a reduction in light detection efficiency. Numerical values and materials mentioned in the present embodiment are illustrated by way of example. They are not necessarily limited to the illustrated ones. Many widely different embodiments of the invention may be configured without departing from the spirit and the scope of the present invention. It should be understood that the present invention is not limited to the specific embodiments described in the specification, except as defined in the appended claims.

What is claimed is:

1. A light detector comprising:
    a plurality of light receiving sections which are formed in a substrate and generate signal charges corresponding to the amount of incident light; and
    a plurality of wirings which are formed on the substrate and fetch the signal charges from the light receiving sections,
    wherein some of the plurality of wirings are disposed so as to overlap with other light receiving sections different from the light receiving sections connected to fetch the signal charges.

2. The light detector according to claim 1, wherein the light receiving sections are arranged in matrix form.

3. The light detector according to claim 2, wherein other wirings of the plurality of wirings are respectively disposed among the light receiving sections arranged in matrix form.

4. The light detector according to claim 3, wherein the wirings connected to the light receiving sections are drawn to one end or the other end of the substrate with a central portion of a matrix as a boundary.

5. The light detector according to claim 4, wherein the wirings connected to the light receiving sections located on the center side of the matrix are drawn to the end of the substrate so as to extend among the light receiving sections, and
    wherein the wirings connected to the light receiving sections located on the end side of the matrix are drawn to the end of the substrate in an extended form so as to overlap with other light receiving sections.

6. A radiation detector comprising:
    a plurality of light receiving sections which are formed in a substrate and generate signal charges corresponding to the amount of incident light;
    a plurality of wirings which are formed on the substrate and fetch the signal charges from the light receiving sections; and
    scintillators which are provided on the light receiving sections of the substrate and emit lights each having a wavelength longer than that of radiation in accordance with the incidence of the radiation,
    wherein some of the plurality of wirings are disposed so as to overlap with other light receiving sections different from the light receiving sections connected to fetch the signal charges.

7. The radiation detector according to claim 6, wherein the light receiving sections are arranged in matrix form.

8. The radiation detector according to claim 7, wherein other wirings of the plurality of wirings are respectively disposed among the light receiving sections arranged in matrix form.

9. The radiation detector according to claim 8, wherein the wirings connected to the light receiving sections are drawn to one end or the other end of the substrate with a central portion of a matrix as a boundary.

10. The radiation detector according to claim 9, wherein the wirings connected to the light receiving sections located on the center side of the matrix are drawn to the end of the substrate so as to extend among the light receiving sections, and
    wherein the wirings connected to the light receiving sections located on the end side of the matrix are drawn to the end of the substrate in an extended form so as to overlap with other light receiving sections.

11. The radiation detector according to claim 6, further comprising a reflection layer which covers the scintillators and reflects the lights emitted from the scintillators to the light receiving sections.

12. A radiation tomography apparatus comprising:
    a radiation irradiating device which irradiates a subject with radiation; and a radiation detector which detects the radiation transmitted through the subject, said radiation detector including, a plurality of light receiving sections which are formed in a substrate and generate signal charges corresponding to the amount of incident light;

a plurality of wirings which are formed on the substrate and fetch the signal charges from the light receiving sections; and scintillators which are provided on the light receiving sections of the substrate and emit lights each having a wavelength longer than that of the radiation in accordance with the incidence of the radiation, wherein some of the plurality of wirings are disposed so as to overlap with other light receiving sections different from the light receiving sections connected to fetch the signal charges.

13. The radiation tomography apparatus according to claim 12, wherein the light receiving sections are arranged in matrix form.

14. The radiation tomography apparatus according to claim 13, wherein other wirings of the plurality of wirings are respectively disposed among the light receiving sections arranged in matrix form.

15. The radiation tomography apparatus according to claim 14, wherein the wirings connected to the light receiving sections are drawn to one end or the other end of the substrate with a central portion of a matrix as a boundary.

16. The radiation tomography apparatus according to claim 15, wherein the wirings connected to the light receiving sections located on the center side of the matrix are drawn to the end of the substrate so as to extend among the light receiving sections, and wherein the wirings connected to the light receiving sections located on the end side of the matrix are drawn to the end of the substrate in an extended form so as to overlap with other light receiving sections.

* * * * *